United States Patent [19]

Larm et al.

[11] Patent Number: 5,885,647
[45] Date of Patent: Mar. 23, 1999

[54] COATING PROCESS

[75] Inventors: Olle Larm, Bromma; Ibrahim Gouda, Sollentuna, both of Sweden

[73] Assignee: Medicarb AB, Bromma, Sweden

[21] Appl. No.: 836,745

[22] PCT Filed: Dec. 5, 1995

[86] PCT No.: PCT/SE95/01459

§ 371 Date: May 20, 1997

§ 102(e) Date: May 20, 1997

[87] PCT Pub. No.: WO96/18423

PCT Pub. Date: Jun. 20, 1996

[30] Foreign Application Priority Data

Dec. 14, 1994 [SE] Sweden .................................. 9404362

[51] Int. Cl.$^6$ ................. B05D 3/10; A61F 2/16
[52] U.S. Cl. .................. 427/2.24; 427/338; 427/322; 427/414; 427/2.13; 427/307
[58] Field of Search .................. 427/2.24, 338, 427/339, 164, 322, 414, 2.13, 307

[56] References Cited

U.S. PATENT DOCUMENTS

| | | | |
|---|---|---|---|
| 4,265,927 | 5/1981 | Ericksson et al. | 427/2.3 |
| 4,326,532 | 4/1982 | Hammar | 427/339 |
| 4,478,914 | 10/1984 | Giese . | |
| 4,613,517 | 9/1986 | Williams et al. | 427/2.24 |
| 4,663,233 | 5/1987 | Beavers | 427/164 |
| 4,810,784 | 3/1989 | Larm | 536/20 |
| 4,876,126 | 10/1989 | Takemura et al. | 428/35.7 |
| 5,023,114 | 6/1991 | Halpern et al. | 427/2.26 |
| 5,049,403 | 9/1991 | Larm et al. | 427/2 |
| 5,057,313 | 10/1991 | Shih | 424/85.91 |
| 5,069,899 | 12/1991 | Whitbourne et al. | 424/56 |
| 5,080,924 | 1/1992 | Kamel et al. | 427/2.24 |
| 5,104,976 | 4/1992 | Casellas et al. | 530/391.9 |
| 5,258,501 | 11/1993 | Barbaric et al. | 530/395 |
| 5,274,119 | 12/1993 | Frazier et al. | 548/521 |
| 5,443,953 | 8/1995 | Hansen et al. | 424/1.49 |
| 5,521,290 | 5/1996 | Sivam et al. | 530/391.5 |
| 5,532,352 | 7/1996 | Pliura et al. | 540/145 |
| 5,571,166 | 11/1996 | Dinh et al. | 623/1 |
| 5,614,487 | 3/1997 | Battersby et al. | 514/2 |
| 5,668,193 | 9/1997 | Gouda et al. | 523/112 |
| 5,672,638 | 9/1997 | Verhoeven et al. | 427/2.25 |
| 5,677,276 | 10/1997 | Dickerson et al. | 514/8 |
| 5,728,420 | 3/1998 | Keogh | 427/2.12 |
| 5,795,560 | 8/1998 | Reed | 424/1.49 |

FOREIGN PATENT DOCUMENTS

| | | |
|---|---|---|
| 0 051 354 | 5/1982 | European Pat. Off. . |
| 0 486 294 | 5/1992 | European Pat. Off. . |
| 3938307 | 5/1991 | Germany . |
| WO 94/03530 | 2/1994 | WIPO . |
| WO 94/16750 | 8/1994 | WIPO . |

OTHER PUBLICATIONS

"A New Method for Covalent Coupling of Heparin and Other Glycosaminoglycans to Substances Containing Primary Amino Groups", James Hoffman et al., *Carbohydrate Research*, 117, (1983) pp. 328–331.

*Primary Examiner*—Diana Dudash
*Attorney, Agent, or Firm*—Burns, Doane, Swecker & Mathis, L.L.P.

[57] ABSTRACT

A process for coating of an intraocular lens to impart tissue compatibility thereto, comprising the steps: a) priming said lens using a solution of a polyamine; b) coating the lens treated in step a) above with a solution of a periodate-oxidized polysaccharide selected from heparin, heparain sulphate, and chondroitin sulphate to stabilize said polyamine by covalent and/or ionical cross-linking; c) coating the lens treated in step b) above with a solution of a polyamine; and d) coating the lens treated according to step c) above with a solution of a periodate-oxidized polysaccharide selected from heparin, heparain sulphate, and chondroitin sulphate in the presence of a cyanoborohydride to convert formed labile Schiff's bases to stable secondary amines.

20 Claims, No Drawings

COATING PROCESS

The present invention relates to a process for the coating of intraocular lenses for the purpose of imparting tissue compatibility to said lenses.

BACKGROUND OF THE INVENTION

Any surface of a non-biological origin initiates a sequence of unwanted reactions when brought into contact with living tissue or blood. The most well known reactions are those generated by the blood-contacting materials that activate the platelets and the plasma coagulation system leading the formation of a thrombus. Foreign surfaces in living tissue activate the complement and the mononuclear cellsystems, thereby creating inflammatory reactions.

Although the present invention is based on the use of polysaccharides selected from heparin, heparan sulphate and chondroitin sulphate for the purpose of providing stable, biocompatible coatings on intraocular eye lenses, the following discussion and disclosure will be mainly directed to heparin or heparan sulphate. However, it is important to note that the invention is not restricted to these two polysaccharides.

Inmobilisation of the blood-anticoagulant, heparin, to artificial, blood-contacting materials has proven to be a successful approach for achieving a thromboresistant surface suitable for short term use (days and weeks). In tis procedure, the structure characteristics of the endothelial lining of the vascular wall are mimiced by end-point attachment of heparin to the surface.

The surface, prepared by end-point attachment of heparin to a polyamine has the following properties: 1) it is nonthrombogenic, 2) it does not activate the complement system, 3) it does not activate the mononuclear cell system, 4) it adheres and stabilizes growth factors and 5) in general it adheres cells to a much lower extent than other surfaces.

Examples on other products where biocompatible coatings are desired are eye lenses, breast implants, vascular grafts, hip joints etc. The surface in question is excellent also for blood contacting materials.

There are several publications that have described the antiproliferative effect of heparin and heparan sulphate on a number of different cells (smooth muscle cells, epithelial cells). In other publications the growth factor stabilizing and activating effect of heparin has been described.

It is now generally agreed that low molecular weight heparin (less than about 2500 D) inhibits cell growth, whereas high molecular weight heparin (higher than about 6000 D) stimulates cell growth.

SUMMARY OF THE INVENTION

The main object of the present invention is to provide a new process for the coating of intraocular lenses to impart tissue compatibility to such lenses.

Another object of the invention is to provide a process for forming a stable coating on intraocular lenses.

A further object of the invention is to provide a process for the attachment of biologically active polysaccharides to the surface of intraocular lenses in such a manner as to inhibit substantial cell growth.

For these and other purposes that will be clear from the following disclosure the invention provides for a process for the coating of an intraocular lens for the purpose of imparting tissue compatibility thereto. Said process involves the following steps:

a) priming said lens using a solution of a polyamine;

b) coating the lens treated in step a) above with a solution of a periodate-oxidized polysaccharide selected from heparin, heparan sulphate, and chondroitin sulphate to stabilize said polyamine by covalent and/or ionical crosslinking;

c) coating the lens treated in step b) above with a solution of a polyamine; and d) coating the lens treated according to step c) above with a solution of a periodate-oxidized polysaccharide selected from heparin, heparan sulphate, and chondroitin sulphate in the presence of a cyancborohydride to convert formed labile Schiff's bases to stable secondary amines.

In the instant disclosure the expression "Polyamine" is intended to cover arm polyamines, including amine-containing polysaccharides, such as chitosan. Chitosan is a linear, 1,4-linked polysaccharide composed of $\beta$-D-glucoseamine units of which some are N-acetylated. Chitosan is made by N-deacetylation of chitin, a polymer present in the shell of inter alia insects and crayfish. The degree of N-deacetylation can be controlled by hydrolysis with the use of alkali. In the present case chitosan is used in the form of commercially available hydrochloride salts having a degree of deacetylation of from about 20 to about 85%.

The preferred periodate-oxidized polysaccharide is heparin or heparan sulphate, said polysaccharides being proteoglycans.

Preferred polyamines are polyethyleneimines or chitosan of varying degrees of N-deacetylation. Said polyamine is suitably present in an aqueous solution in a concentration of from about 0.01 to about 0.1% by weight.

The periodate-oxidized polysaccharide is preferably present in an aqueous solution, for example in a concentration of about 0.01 to about 0.1% by weight, it being preferred that the pH of said solution is from about 3 to out 5.

The cyanoborohydride used in combination with the periodate-oxidized polysaccharide is preferably an alkalimetal cyanoborohydride, such as sodium cyanoborohydride.

Step d) of the process defined above is preferably performed at an increased temperature, such as from about room temperature up to boiling, preferably from about 40° C. to about 75° C., such as from about 50° C. to about 70° C.

In the process defined above it is preferred that step b) is repeated between steps c) and d), and step a) is suitably repeated after step b) thus repeated.

In the process according to the present invention the solution used in step a) above may also contain crotonaldehyde at a basic pH, such as between about 8 to about 10. Said pH can be maintained using a buffer or a base, such as borate buffer or an alkali metalhydroxide, for example sodiumhydroxide.

According to a preferred embodiment of the process of the present invention the coating of an intraocular lens involves the following steps:

a) priming said lens using a solution of a polyamine and croton aldehyde;

b) coating the lens treated according to step a) above with periodate-oxidized heparin or heparan sulphate to stabilize said polyamine;

c) repeating step a) above on the lens treated according to step b) above;

d) repeating step b) above on the lens treated in accordance with step c) above;

e) treating the lens resulting from step d) above using a solution of a polyamine; and f) coating the lens treated in accordance with step e) above with a solution of periodate-oxidized heparin or heparan sulphate in the presence of a cyanoborohydride to convert formed labile Schiff's bases to stable secondary amines.

In order to facilitate priming of the intraocular lens it is preferred to etch the lens before starting the priming thereof, such etching suitably being performed with an oxidizing agent, for example ammoniumperoxidisulphate in aqueous solution, or any other oxidizing agent suitable for the intended purpose. Since the surface of intraocular lenses to be treated in accordance with the present invention usually are of a hydrophobic nature, such etching step in advance of the priming procedure is preferred to improve adherence of the priming agent to the surface of the lens.

SPECIFIC EMBODIMENTS OF THE PROCESS

To improve the understanding of the present invention it will now be further illustrated below by non-limiting examples, wherein percentages are by weight unless otherwise defined.

PREPARATION OF SOLUTIONS

EXAMPLE 1

Preparation of Polymine Solution 500 mL of borate buffer in aqueous solution, pH 9.0, are prepared by dissolving boric acid, sodiumhydroxide pellets and sodiumchloride in water. To said buffer solution there is added 0.5 mL of polymine, 5% in water, and 170 µL of crotonaldehyde. The solution thus prepared is designated L1.

EXAMPLE 2

An aqueous polymine solution is prepared by adding 5 mL of a 5% polymine solution to 500 mL of distilled water. The pH of the resulting solution is adjusted to 9.0 using 0.5M sodiumhydroxide. The solution thus prepared is designated L3.

EXAMPLE 3

A solution of sodiumperiodate-oxidized sodiumheparin is prepared in the following manner.

1.0 g of sodiumperiodate, $NaIO_4$, is dissolved in 200 mL of distilled water. 10 g of sodiumheparin is added to the solution of sodiumperiodate and is set aside over night in the dark with stirring. The resulting solution, after adding 10 mL of glycerol thereto and stirring for 2 h, is dialyzed against water, the water being exchanged every other hour. This results in a solution containing periodate-oxidized heparin in a concentration of about 19 mg/mL. This solution is designated L2.

EXAMPLE 4

To 500 mL of distilled water there is added 4.4 g sodiumchloride and 7 mL of solution L2 prepared in Example 3. The pH of the solution is adjusted to 3.9 using 0.5M hydrochloric acid. The resulting solution is designated L4:1.

EXAMPLE 5

To 500 mL distilled water there is added 4.4 g sodiumchloride, 7 mL of solution L2 from Example 3, and the pH of the solution is adjusted to 3.9 using 0.5M hydrochloric acid. The temperature of the solution is then raised to 55° C. and 15 mg sodiumcyanoborohydride is added thereto. The resulting solution is designated L4:2.

Coating of Intraocular Lenses

The intraocular lenses used in the following examples are based on polymethylmethacrylate (PMMA), but the invention is equally applicable to other materials, such as polysiloxane, for example poly(dimethylsiloxane) (PDMS), poly(dimethyldiphenylsiloxane) (PDMDPS), or hydrophilic acrylics, such as polyhydroxiethylmethacrylate. Another type of useful material is constituted by hydrophobic acrylics with a low glass transition temperature, such as a mixture of acrylate and methacrylate. An example of such material is copolymers of ethylphenylacrylates and ethylphenylmethacrylate. Such polymers have a glass transition temperature at about room temperature.

EXAMPLE 6

Using the solutions prepared in Examples 1–5 intraocular lenses based on polymethylmethacrylate are treated in the following manner.

Initially, the lenses are etched using a 5% ammonium peroxidisulphate aqueous solution at 60° C. for 30 minutes. After rinsing with distilled water the etched lenses are then treated by immersion in solution L1 from Example 1 for 10 minutes at room temperature to provide priming of the lens. After rinsing with distilled water the lens is then immersed in solution L4:1 of Example 4 for 10 minutes at room temperature, and after rinsing with distilled water treatment of the lens with solution L1 from Example 1 is repeated in the same manner as above. Again, after rinsing the lens with distilled water it is finally treated by immersion into solution L4:2 from Example 5, said solution being heated to a temperature of 55° C. and the lens is kept in the solution for 2 h. After a final rinsing of the lens with distilled water it is now provided with a stable coating imparting tissue compatibility of the lens, and by multipoint attachment of the heparin molecules to the surface of the lens, cell growth is inhibited corresponding to the use of a low molecular weight heparin having a molecular weight of less than about 2500 D.

EXAMPLE 7

Example 6 is repeated but in this case the steps of treatment for 10 minutes at room temperature with solution L4:1 and then a treatment for 10 minutes at room temperature using solution L3 are introduced. The lens is then treated with solution L4:2 and the procedure is concluded as in Example 6. After every treatment step the lens is rinsed with distilled water.

EXAMPLE 8

Example 6 is repeated but using instead of solutions L1 and L3 as per Example 6, an alternative solution L5 containing chitosan as a primer. Said solution. L5 is prepared in the following manner.

An aqueous solution of the hydrochloride salt of chitosan is prepared by dissolving chitosan having a degree of N-deacetylation of about 85% in water to a concentration of 0.25% w/v, the solution being adjusted to pH 5.0 using hydrochloric acid. The presence of amino groups on the intraocular lens primed with solution L5 is verified with an indicator (ponceau S, Sigma).

Using a chitosan solution for priming of the lens results in similar advantageous properties of the coated lens as those obtained in Example 6.

EXAMPLE 9

Example 7 is repeated but using solution L5 of Example 8 instead of solutions L1 and L3 used in Example 6. Similar results are obtained.

We claim:

1. A process for the coating of an intraocular lens to impart tissue compatibility thereto, comprising the steps:
    a) priming said lens using a solution of a polyamine;
    b) coating the lens treated in step a) above with a solution of a periodate-oxidized polysaccharide selected from heparin, heparan sulphate, and chondroitin sulphate to stabilize said polyamine by covalent and/or ionical crosslinking;
    c) coating the lens treated in step b) above with a solution of a polyamine; and
    d) coating the lens treated according to step c) above with a solution of a periodate-oxidized polysaccharide selected from heparin, heparan sulphate, and chondroitin sulphate in the presence of a cyanoborohydride to convert formed labile Schiff's bases to stable secondary amines.

2. A process according to claim 1, wherein said polyamine is a polyethyleneimine or chitosan.

3. A process according to claim 1, wherein said polyamine is present in an aqueous solution in a concentration of from about 0.01 to about 0.1% by weight.

4. A process according to claim 1, wherein said periodate oxidized polysaccharide is present in an aqueous solution in a concentration of about 0.01 to about 0.1% by weight, the pH of said solution being from about 3 to about 5.

5. A process according to claim 1, wherein said cyanoborohydride is sodium cyanoborohydride.

6. A process according to claim 1, wherein step d) above is performed at an increased temperature, from about room temperature up to boiling, preferably from about 40° C. to about 75° C.

7. A process according to claim 1, wherein step b) is repeated between steps c) and d).

8. A process according to claim 7, wherein step a) is repeated after repeated step b).

9. A process according to claim 1, wherein the solution used in step a) also contains croton aldehyde at a basic pH, such as between about 8 and about 10.

10. A process according to claim 9, wherein the pH is maintained using a buffer or a base.

11. A process for the coating of an intraocular lens to impart tissue compatibility to said lens, comprising the steps:
    a) priming said lens using a solution of a polyamine and croton aldehyde;
    b) coating the lens treated according to step a) above with periodate-oxidized heparin or heparan sulphate to stabilize said polyamine;
    c) repeating step a) above on the lens treated according to step b) above;
    d) repeating step b) above on the lens treated in accordance with step c) above;
    e) treating the lens resulting from step d) above using a solution of a polyamine; and
    f) coating the lens treated in accordance with step e) above with a solution of periodate-oxidized heparin or heparan sulphate in the presence of a cyanoborohydride to convert formed labile Schiff's bases to stable secondary amines.

12. A process according to claim 1, wherein said intraocular lens, before priming in step a), is etched, such as with an oxidizing agent, for example ammonium peroxidisulphate in aqueous solution.

13. A process according to claim 2, wherein said polyamine is present in an aqueous solution in a concentration of from about 0.01 to about 0.1% by weight.

14. A process according to claim 2, wherein said periodate oxidized polysaccharide is present in an aqueous solution in a concentration of about 0.01 to about 0.1% by weight, the pH of said solution being from about 3 to about 5.

15. A process according to claim 3, wherein said periodate oxidized polysaccharide is present in an aqueous solution in a concentration of about 0.01 to about 0.1% by weight, the pH of said solution being from about 3 to about 5.

16. A process according to claim 2, wherein said cyanoborohydride is sodium cyanoborohydride.

17. A process according to claim 2, wherein step d) above is performed at an increased temperature, from about room temperature up to boiling, preferably from about 40° to about 75° C.

18. A process according to claim 2, wherein step b) is repeated between steps c) and d).

19. A process according to claim 2, wherein the solution used in step a) also contains croton aldehyde at a basic pH, such as between about 8 and about 10.

20. A process according to claim 11, wherein said intraocular lens, before priming in step a), is etched, such as with an oxidizing agent, for example ammonium peroxidisulphate in an aqueous solution.

* * * * *